United States Patent [19]

Bowles et al.

[11] Patent Number: 5,180,724
[45] Date of Patent: Jan. 19, 1993

[54] CARBOXAMIDE AMINO ACID HETEROBICYCLIC PAF ANTAGONISTS

[75] Inventors: Stephen A. Bowles, Tring; Mark Whittaker, Old Marston; Andrew Miller, Headington, all of England

[73] Assignee: British Bio-Technology Limited, Oxford, England

[21] Appl. No.: 760,174

[22] Filed: Sep. 16, 1991

[30] Foreign Application Priority Data

Apr. 9, 1991 [GB] United Kingdom ................ 9107398

[51] Int. Cl.$^5$ .................. C07D 471/04; C07D 235/08; A61K 31/435; A61K 31/415
[52] U.S. Cl. .................................... 514/248; 514/303; 514/394; 514/395; 514/293; 544/236; 546/82; 546/118; 548/302.1; 548/310.7; 548/310.4; 548/310.1; 548/307.1; 548/306.4; 548/304.4; 548/306.1
[58] Field of Search ............... 546/82, 118; 544/236; 548/325, 326, 329, 330, 332, 333, 334; 514/303, 248, 394, 395, 293

[56] References Cited

U.S. PATENT DOCUMENTS 4,804,658  2/1989  Manley et al. ...................... 546/118

FOREIGN PATENT DOCUMENTS

89/08653  9/1989  World Int. Prop. O.
90/09997  9/1990  World Int. Prop. O. .......... 548/325

Primary Examiner—Bernard Dentz
Attorney, Agent, or Firm—Allegretti & Witcoff, Ltd.

[57] ABSTRACT

Compounds of general formula I;

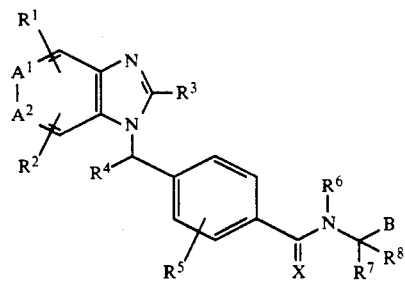

wherein
$R^1$, $R^2$, $R^3$, $R^4$, $R^5$, $R^6$, $R^7$, $R^8$, $A^1$, $A^2$, B, and X are variables.

These compounds are antagonists of platelet activating factor (PAF) and as such are useful in the treatment or amelioration of various diseases or disorders mediated by PAF.

19 Claims, No Drawings

CARBOXAMIDE AMINO ACID HETEROBICYCLIC PAF ANTAGONISTS

This invention relates primarily to novel compounds which are antagonists of platelet activating factor.

Platelet Activating Factor (PAF) is a bioactive phospholipid which has been identified as 1-0-hexadecyl/octadecyl-2-acetyl-sn-glyceryl-3-phosphoryl choline. PAF is released directly from cell membranes and mediates a range of potent and specific effects on target cells resulting in a variety of physiological responses which include hypotension, thrombocytopenia, bronchoconstriction, circulatory shock, and increased vascular permeability (oedema/erythema). It is known that these physiological effects occur in many inflammatory and allergic diseases and PAF has been found to be involved in a number of such conditions including asthma, endotoxin shock, glomerulonephritis, immune regulation, transplant rejection, gastric ulceration, psoriasis, embryo implantation and cerebral, myocardial and renal ischemia. Thus the compounds of the invention, by virtue of their ability to antagonise the actions of PAF, should be of value in the treatment of any of the above conditions.

Compounds which have been disclosed as possessing activity as PAF antagonists include compounds which are structurally related to the PAF molecule such as glycerol derivatives (EP-A-0238202), and heterocyclic compounds such as 2,5-diaryl tetrahydrofurans (EP-A-0144804) and imidazopyridine derivatives (EP-A-0260613 and WO-A-8908653).

The present invention provides novel and useful substituted amino acid derivatives and their pharmaceutically acceptable acid addition salts, and pharmaceutical uses thereof as PAF antagonists.

According to a first aspect of the invention there is provided a compound of general formula I;

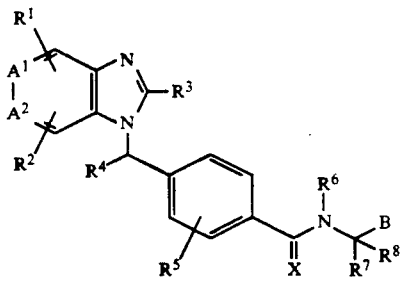

wherein:
$A^1$ is =N—, =CH— or =CR$^1$—;
$A^2$ is —N▽, —CH= or —CR$^2$=;
each of $R^1$ and $R^2$ independently represents hydrogen, $C_1$-$C_6$ alkyl, $C_2$-$C_6$ alkenyl, halogen, CN, $CO_2H$, $CO_2C_1$-$C_6$ alkyl, $CONH_2$, CHO, $CH_2OH$, $CF_3$, $C_1$-$C_6$ alkoxy, $C_1$-$C_6$ alkylthio, $SOC_1$-$C_6$ alkyl, $SO_2C_1$-$C_6$ alkyl, $NH_2$, NHCOMe or $NO_2$ or $R^1$ and $R^2$ together with the carbon atoms to which they are attached form a fused phenyl ring;
$R^3$ represents hydrogen, $C_1$-$C_6$ alkyl, $C_2$-$C_6$ alkenyl, $C_1$-$C_6$ alkoxy, $C_1$-$C_6$ alkylthio, $C_1$-$C_6$ alkoxy ($C_1$-$C_6$ alkyl), $C_1$-$C_6$ alkylthio ($C_1$-$C_6$ alkyl), $CF_3$, phenyl ($C_1$-$C_6$ alkyl), $C_3$-$C_8$ cycloalkyl or thiophenyl;
$R^4$ represents hydrogen, $C_1$-$C_6$ alkyl, $C_2$-$C_6$ alkenyl, $CO_2C_1$-$C_6$ alkyl, $C_1$-$C_6$ alkylthio, $C_1$-$C_6$ alkylthio ($C_1$-$C_6$ alkyl), $C_1$-$C_6$ alkoxy ($C_1$-$C_6$ alkyl), phenyl ($C_1$-$C_6$ alkyl) or thiophenyl;
$R^5$ represents hydrogen, $C_1$-$C_6$ alkyl, $C_2$-$C_6$ alkenyl, halogen or $C_1$-$C_6$ alkoxy;
X represents an oxygen or a sulphur atom;
$R^6$ represents hydrogen, $C_1$-$C_6$ alkyl, $C_2$-$C_6$ alkenyl, $COC_1$-$C_6$ alkyl, $C_1$-$C_6$ alkoxy ($C_1$-$C_6$ alkyl), $C_3$-$C_8$ cycloalkyl, $C_4$-$C_8$ cycloalkenyl or a group D wherein D represents a group:

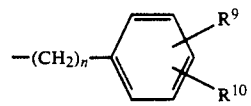

wherein n is an integer from 0 to 3, and each of $R^9$ and $R^{10}$ is independently hydrogen, $C_1$-$C_6$ alkyl, $C_2$-$C_6$ alkenyl, halogen, CN, $CO_2H$, $CO_2C_1$-$C_6$ alkyl, $CONH_2$, CHO, $CH_2OH$, $CF_3$, $C_1$-$C_6$ alkoxy, $C_1$-$C_6$ alkylthio, $SOC_1$-$C_6$ alkyl, $SO_2C_1$-$C_6$ alkyl, $NH_2$ or NHCOMe;
or $R^6$ together with $R^7$ and the atoms to which they are attached forms a 5 to 8 membered nitrogen-containing heterocyclic ring;
each of $R^7$ and $R^8$ independently represents hydrogen, $C_1$-$C_6$ alkyl, $C_2$-$C_6$ alkenyl, $CO_2C_1$-$C_6$ alkyl ($C_1$-$C_6$ alkyl), $C_1$-$C_6$ alkylthio ($C_1$-$C_6$ alkyl), $C_1$-$C_6$ alkoxy ($C_1$-$C_6$ alkyl), benzoxy ($C_1$-$C_6$ alkyl), a side chain of a naturally occurring amino acid or a group D as defined above;
or $R^7$ together with $R^8$ and the atoms to which they are attached forms a 5 to 8 membered nitrogen-containing heterocyclic ring;
or $R^7$ and $R^8$ together with the carbon atom to which they are attached form a $C_3$-$C_8$ cycloalkyl ring;
B represents a) a $ZR^{11}$ group wherein Z is —C(=O)—, —C(=O)O—, —CH$_2$O—, —CH$_2$OC(=O)—, —C(=S)—, —C(=S)—, —C(=S)O— or —CH$_2$S— and $R^{11}$ is $C_1$-$C_{18}$ alkyl, $C_2$-$C_{18}$ alkenyl, $C_1$-$C_6$ alkoxy ($C_1$-$C_6$ alkyl), $C_1$-$C_6$ alkylthio ($C_1$-$C_6$ alkyl), $C_1$-$C_6$ alkoxy ($CH_2CH_2OCH_2CH_2$), $C_3$-$C_8$ cycloalkyl, $C_4$-$C_8$ cycloalkenyl, pyridyl or a group D as defined above;
b) a $CH_2NR^{12}R^{13}$ group or a $CONR^{12}R^{13}$ group wherein each of $R^{12}$ and $R^{13}$ is independently hydrogen, $C_1$-$C_6$ alkyl, $C_3$-$C_8$ cycloalkyl, pyridyl, a group D as defined above or $R^{12}$ and $R^{13}$ together with the nitrogen atom to which they are attached form a 5 to 8 membered nitrogen-containing heterocyclic ring; c) a 5- or 6-membered aromatic heterocyclic ring containing one or more heteroatoms selected from nitrogen, oxygen and sulphur and the ring may be optionally substituted with one or more substituents selected from $C_1$-$C_6$ alkyl, $C_1$-$C_6$ alkoxy, halogen, $CF_3$ and CN;
or a pharmaceutically or veterinarily acceptable acid addition salt or hydrate thereof.

Hereafter in this specification the term "compound" includes "salt" or "hydrate" unless the context requires otherwise.

As used herein the term "halogen" or its abbreviation "halo" means fluoro, chloro, bromo or iodo.

As used herein the term "$C_1$-$C_6$ alkyl" refers to straight chain or branched chain hydrocarbon groups having from one to six carbon atoms. Illustrative of such alkyl groups are methyl, ethyl, propyl, isopropyl, butyl, isobutyl, sec-butyl, tert-butyl, pentyl, neopentyl and hexyl.

As used herein the term "$C_1$-$C_{18}$ alkyl" refers to straight chain or branched chain hydrocarbon groups having from one to eighteen carbon atoms. Illustrative of such alkyl groups are methyl, ethyl, propyl, isopropyl, butyl, isobutyl, sec-butyl, tert-butyl, pentyl, neopentyl, hexyl, decyl, dodecyl, tridecyl, tetradecyl, pentadecyl, hexadecyl, heptadecyl, and octadecyl. From one to six carbon atoms may be preferred.

As used herein the term "$C_2$-$C_6$ alkenyl" refers to straight chain or branched chain hydrocarbon groups having from two to six carbon atoms and having in addition one double bond, of either E or Z stereochemistry where applicable. This term would include for example, vinyl, 1-propenyl, 1- and 2-butenyl and 2-methyl-2-propenyl.

As used herein the term "$C_2$-$C_{18}$ alkenyl" refers to straight chain or branched chain hydrocarbon groups having from two to eighteen carbon atoms and having in addition one or more double bonds, of either, E or Z stereochemistry where applicable. This term would include for example, vinyl, 1-propenyl, 1- and 2-butenyl, 2-methyl-2-propenyl, geranyl, and farnesyl. From two to six carbon atoms may be preferred.

As used herein the term "$C_1$-$C_6$ alkoxy" refers to straight chain or branched chain alkoxy groups having from one to six carbon atoms. Illustrative of such alkoxy groups are methoxy, ethoxy, propoxy, isopropoxy, butoxy, isobutoxy, sec-butoxy, tert-butoxy, pentoxy, neopentoxy and hexoxy.

As used herein the term "$C_1$-$C_6$ alkylthio" refers to straight chain or branched chain alkylthio groups having from one to six carbon atoms. Illustrative of such alkyl groups are methylthio, ethylthio, propylthio, isopropylthio, butylthio, isobutylthio, sec-butylthio, tert-butylthio, pentylthio, neopentylthio and hexylthio.

As used herein, the term "$C_3$-$C_8$ cycloalkyl" refers to an alicyclic group having from 3 to 8 carbon atoms. Illustrative of such cycloalkyl groups are cyclopropyl, cyclobutyl, cyclopentyl and cyclohexyl.

As used herein, the term "$C_4$-$C_8$ cycloalkenyl" refers to an alicyclic group having from 4 to 8 carbon atoms and having in addition one or more double bonds. Illustrative of such cycloalkenyl groups are cyclopentenyl, cyclohexenyl, cycloheptenyl and cyclooctenyl.

As used herein, the term "nitrogen-containing heterocyclic ring" refers to an aromatic or alicyclic ring comprising one or more nitrogen atoms and optionally one or more other heteroatoms. Illustrative of such rings are pyrrolidine, piperidine, hexamethyleneimine, heptamethylenimine, morpholine and piperazine.

In compounds of this invention, the presence of several asymmetric carbon atoms gives rise to diastereoisomers, each of which consists of two enantiomers, with the appropriate R or S stereochemistry at each chiral center. The invention is understood to include all such diastereoisomers, their optically active enantiomers and mixtures thereof.

The term "pharmaceutically or veterinarily acceptable acid addition salt" refers to a salt prepared by contacting a compound of formula (I) with an acid whose anion is generally considered suitable for human or animal consumption.

Examples of pharmaceutically and/or veterinarily acceptable acid addition salts include the hydrochloride, sulphate, phosphate, acetate, propionate, lactate, maleate, succinate and tartrate salts.

Preferred compounds include those in which, independently or in any compatible combination:

$A^1$ represents =N— or =CH—;
$A^2$ represents —N= or —CH=;
$R^1$ represents a hydrogen atom;
$R^2$ represents a hydrogen atom;
$R^3$ represents a $C_1$-$C_6$ alkyl (for example methyl) group;
$R^4$ represents a hydrogen atom;
$R^5$ represents a hydrogen atom;
X represents an oxygen atom;
$R^6$ represents a $C_1$-$C_6$ alkyl (for example methyl) group;
$R^7$ represents the side chain of a naturally occurring amino acid;
$R^8$ represents a hydrogen atom;
when $R^7$ represents the side chain of a naturally occurring amino acid the stereochemistry of the carbon atom to which $R^7$ and $R^8$ are attached is the same as that of the naturally occurring amino acid;
B represents a $ZR^{11}$ group;
Z represents a —C(=O)O— group or a —$CH_2$O— group;
$R^{11}$ represents a $C_1$-$C_{18}$ alkyl (for example methyl or ethyl) group or a group D.

Preferred side chains of naturally occurring amino acids include the side chain of leucine.

Particularly preferred compounds include:
1. (A) N-Methyl-L-leucinyl methyl ester 4-(3H-2-methylimidazo-[4,5-c]pyridylmethyl)benzamide,
   (B) N-Methyl-L-leucinyl methyl ester 4-(1H-2-methylimidazo-[4,5-c]pyridylmethyl)benzamide,
2. (A) N-Methyl-L-leucinyl ethyl ester 4-(3H-2-methylimidazo-[4,5-c]pyridylmethyl)benzamide,
   (B) N-Methyl-L-leucinyl ethyl ester 4-(1H-2-methylimidazo-[4,5-c]pyridylmethyl)benzamide,
3. (A) N-Methyl-L-leucinol ethyl ether 4-(3H-2-methylimidazo-[4,5-c]pyridylmethyl)benzamide,
   (B) N-Methyl-L-leucinol ethyl ether 4-(1H-2-methylimidazo-[4,5-c]pyridylmethyl)benzamide.

Compounds of general formula I may be prepared by any suitable method known in the art and/or by the following process, which itself forms part of the invention.

According to a second aspect of the invention, there is provided a process for preparing a compound of general formula I as defined above, the process comprising:

(a) treating an imidazole derivative represented by general formula II

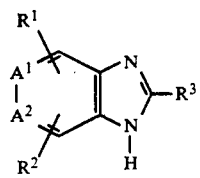

II wherein $A^1$, $A^2$, $R^1$, $R^2$ and $R^3$ are as defined in general formula I, with a suitable base (e.g. sodium hydride, potassium hydride or sodium bis(trimethylsilyl)amide), followed by a compound of general formula III

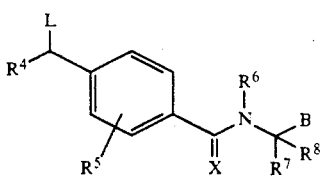

wherein $R^4$, $R^5$, X, $R^6$, $R^7$, $R^8$ and B are as defined in general formula I, and L is chloro, bromo, iodo, methanesulphonyloxy, p-toluenesulphonyloxy or trifluoromethanesulphonyloxy; or (b) treating a substituted diamino compound of general formula IV

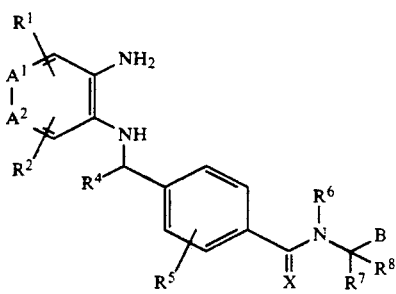

wherein $A^1$, $A^2$, $R^1$, $R^2$, $R^4$, $R^5$, X, $R^6$, $R^7$, $R^8$ and B are as defined in general formula I, with a carboxylic acid of general formula V $$R^3CO_2H \qquad V$$

wherein $R^3$ is as defined in general formula I, or a suitable derivative thereof; and (c) optionally after step (a) or step (b) converting, in one or a plurality of steps, a compound of general formula I into another compound of general formula I.

The reaction of step (a) can for preference be conducted in an aprotic solvent, preferably tetrahydrofuran, to yield compounds of general formula I. In the case where an unsymmetrically substituted imidazole derivative is used the reaction can yield an isomeric mixture, which is separated by chromatography to yield compounds of general formula I.

In step (b), derivatives of carboxylic acids of general formula V, such as acid halides or trialkylorthoformates are suitable substrates for this reaction. Carboxylic acids of general formula V and derivatives are available in the art or can be prepared by procedures known to those skilled in the art.

By means of step (c) compounds of general formula I wherein B is a $CONR^{12}R^{13}$ group wherein $R^{12}$ and $R^{13}$ are as defined for general formula I, may be prepared by the following methods;

i) by treatment of a compound of general formula I wherein B is a $CO_2R^{11}$ group wherein $R^{11}$ is a benzyl group with hydrogen in the presence of a noble metal catalyst (e.g. 10% palladium on charcoal) to give a carboxylic acid which is then treated with an amine of general formula $HNR^{12}R^{13}$ in the presence of a coupling reagent (e.g. dicyclohexylcarbodiimide);

ii) by treatment of a compound of general formula I wherein B is a $CO_2R^{11}$ group wherein $R^{11}$ is lower alkyl with a dimethylaluminium amide of general formula VI $$(Me)_2AlNR^{12}R^{13} \qquad VI$$

wherein $R^{12}$ and $R^{13}$ are as defined in general formula I, which is prepared in situ from trimethylaluminium and an amine of general formula $HNR^{12}R^{13}$.

Also by means of step (c) certain compounds of general formula I wherein B is a $CO_2R^{11}$ group wherein $R^{11}$ is as defined in general formula I or a $CONR^{12}R^{13}$ group wherein $R^{12}$ and $R^{13}$ are as defined in general formula I but are not hydrogen atoms, may be prepared by treatment of a compound of general formula I wherein $R^6$ is hydrogen with base followed by an electrophile of general formula VII $$LR^6 \qquad VII$$

wherein $R^6$ is as defined in general formula I but is not a hydrogen atom, a phenyl or a substituted phenyl group, and L is chloro, bromo, iodo, methanesulphonyloxy, p-toluenesulphonyloxy or trifluoromethanesulphonyloxy. Electrophiles of general formula VII are available in the art or can be prepared by procedures known to those skilled in the art.

Also by means of step (c) certain compounds of general formula I wherein $R^6$ is as defined in general formula I but is not a hydrogen atom, B is a $CO_2R^{11}$ group wherein $R^{11}$ is as defined in general formula I or a $CONR^{12}R^{13}$ group wherein $R^{12}$ and $R^{13}$ are as defined in general formula I but are not hydrogen atoms, can be prepared by treatment of a compound of general formula I wherein $R^4$ is a hydrogen atom with a suitable base (e.g. sodium bis(trimethylsilyl)amide) in an aprotic solvent (e.g. tetrahydrofuran) followed by an electrophile of the general formula $LR^4$ wherein $R^4$ is $C_1$-$C_6$ alkyl, $C_3$-$C_6$ alkenyl, $CO_2C_1$-$C_6$ alkyl, $C_1$-$C_6$ alkylthio, $C_1$-$C_6$ alkylthio ($C_1$-$C_6$ alkyl), $C_1$-$C_6$ alkoxy ($C_1$-$C_6$ alkyl) or phenyl ($C_1$-$C_6$ alkyl) and L is chloro, bromo, iodo, methanesulphonyloxy, p-toluenesulphonyloxy or trifluoromethanesulphonyloxy. Electrophiles of the general formula $LR^4$ are available in the art or can be prepared by methods analogous to those known in the art.

Also by means of step (c) certain compounds of general formula I wherein X is a sulphur atom, may be prepared by treatment of a compound of general formula I wherein X is an oxygen atom with 2,4-bis(p-methoxyphenyl)-1,3-dithiadiphosphetane-2,4-disulphide (Lawesson's reagent).

Imidazole derivatives of general formula II may be prepared by a number of methods. The first method involves treatment of a 1,2-diamine of general formula VIII

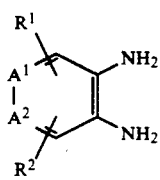

wherein $A^1$, $A^2$, $R^1$ and $R^2$ are as defined in general formula I, with dimethylformamide and a carboxylic acid of general formula V, wherein $R^3$ is as defined in general formula I. Derivatives of carboxylic acids of general formula V, such as acid halides, trialkylorthoformates or imino ether salts are also suitable substrates for this reaction. 1,2-Diamines of general formula VIII are available in the art or may be prepared by the reduction of a 1,2-nitroamine of general formula IX

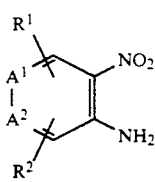

IX wherein $A^1$, $A^2$, $R^1$ and $R^2$ are as in general formula I, for example in the presence of hydrogen and a catalyst such as palladium or platinum.

1,2-Nitroamines of general formula IX are available in the art or can be prepared by methods analogous to those known in the art.

In a second method imidazole derivatives of general formula II may be prepared by the treatment of an 1,2-nitroamide of general formula X

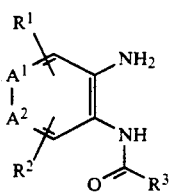

X wherein $A^1$, $A^2$, $R^1$, $R^2$ and $R^3$ are as defined in general formula I, with a suitable reducing agent (e.g. tin in acetic acid).

1,2-Nitroamides of general formula X may be prepared by the treatment of a 1,2-nitroamine of general formula IX with an acid chloride of general formula XI

ClOCR$^3$  XI wherein $R^3$ is as defined in general formula I, in an aprotic solvent and in the presence of a suitable base such as, for example, triethylamine. Alternatively, the reaction may be conducted utilizing a compound of general formula XII $R^3CO_2COR^3$  XII wherein $R^3$ is as defined in general formula I.

Another procedure for preparing 1,2-nitroamides of general formula X involves reaction of a 1,2-nitroamine of general formula IX with a carboxylic acid of general formula V, wherein $R^3$ is as defined in general formula I, in the presence of a coupling reagent (e.g. 1,3-dicyclohexylcarbodiimide). Acid chlorides of general formula XI, acid anhydrides of general formula XII and carboxylic acids of general formula V are available in the art or can be prepared by methods analogous to those known in the art.

Compounds of general formula III may be prepared by treatment of an amine of general formula XIII

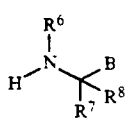

XIII wherein $R^5$, X, $R^6$, $R^7$, $R^8$ and B are as defined in general formula I, with an acid halide of general formula XIV

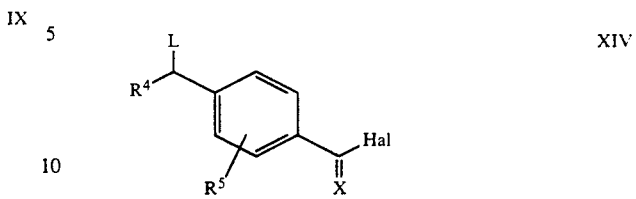

XIV wherein $R^4$ is as defined in general formula I, L is chloro, bromo, iodo, methanesulphonyloxy, p-toluenesulphonyloxy or trifluoromethanesulphonyloxy and Hal is a halide (e.g. fluoro, chloro or bromo), in the presence of a suitable base (e.g. triethylamine). Amines of general formula XIII and sulphonyl halides of general formula XIV are known in the art or may be prepared by methods known in the art.

Substituted 1,2-diamines of general formula IV may be prepared by the reduction of a substituted 1,2-nitroamine of general formula XV

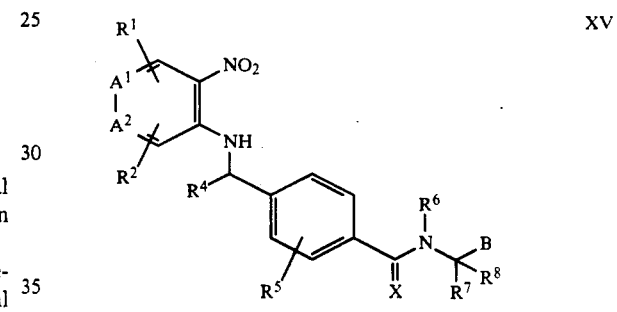

XV wherein $A^1$, $A^2$, $R^1$, $R^2$, $R^4$, $R^5$, X, $R^6$, $R^7$, $R^8$ and B are as in general formula I, for example in the presence of hydrogen and a catalyst such as palladium or platinum.

Substituted 1,2-nitroamines of general formula XV may be prepared by a number of methods. The first of these methods involves the treatment of a nitro compound of general formula XVI

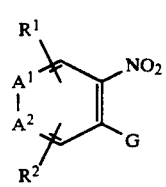

XVI wherein $A^1$, $A^2$, $R^1$ and $R^2$ are as defined in general formula I and G is halo or $C_1$-$C_6$ alkoxy; is treated with a amino compound of general formula XVII

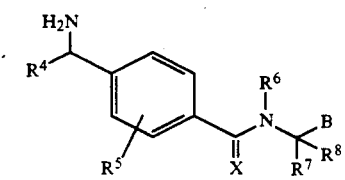

XVII wherein $R^4$, $R^5$, X, $R^6$, $R^7$, $R^8$ and B are as defined in general formula I. Nitro compounds of general formula XVI are available in the art or can be prepared by methods analogous to those known in the art. Amino compounds of general formula XVII can be prepared by treatment of a compound of general formula III with hexamethylenetetramine followed by treatment with ethanolic hydrochloric acid.

A second procedure for the preparation of amino nitrobenzenes of general formula XV involves the reduction of an imino nitro compound of general formula XVIII

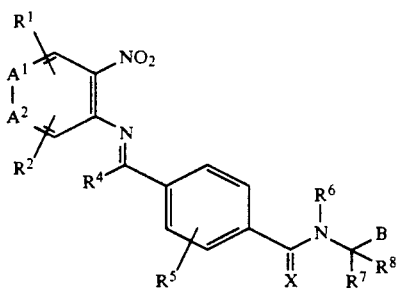

wherein $A^1$, $A^2$, $R^1$, $R^2$, $R^4$, $R^5$, X, $R^6$, $R^7$, $R^8$ and B are as defined in general formula I, for example in the presence of hydrogen and a catalyst such as palladium or platinum.

The imino nitro compounds of general formula XVIII may be prepared by treating a 1,2-nitroamine of general formula IX with a substituted carbonyl derivative of general formula XIX

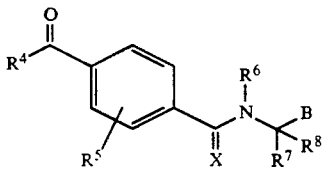

wherein $R^5$, X, $R^6$, $R^7$, $R^8$ and B are as defined in general formula I and $R^4$ is as defined in general formula I but is not a $C_1$–$C_6$ alkylthio group. Substituted carbonyl derivatives of general formula XIX may be prepared by treatment of a compound of general formula III with an oxidizing agent (e.g. dimethyl sulphoxide).

Alternatively nitro amino compounds of general formula XV in which $R^4$ is hydrogen may be prepared by the reduction of a 1,2-nitroamide of general formula XX

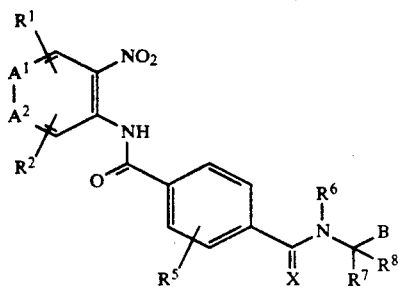

wherein $A^1$, $A^2$, $R^1$, $R^2$, $R^5$, X, $R^6$, $R^7$, $R^8$ and B are as defined in general formula I, with a suitable metal hydride reducing agent such as for example lithium aluminium hydride.

The 1,2-nitroamides of general formula XX may be prepared by the coupling of a 1,2-nitroamine of general formula IX with an acid chloride of general formula XXI

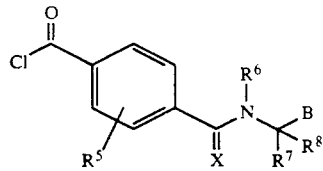

wherein $R^5$, X, $R^6$, $R^7$, $R^8$ and B are as defined in general formula I, in an aprotic solvent and in the presence of a suitable base such as, for example, triethylamine. Alternatively, the reaction may be conducted utilizing an acid anhydride of general formula XXII

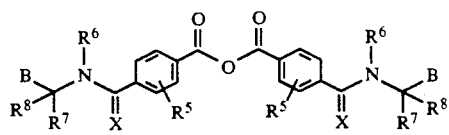

wherein $R^5$, X, $R^6$, $R^7$, $R^8$ and B are as defined in general formula I. Another procedure for preparing 1,2-nitroamides of general formula XX involves reaction of a 1,2-nitroamine of general formula IX with a carboxylic acid of general formula XXIII

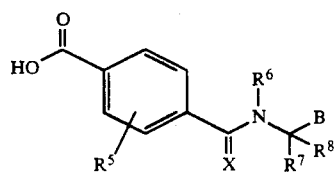

wherein $R^5$, X, $R^6$, $R^7$, $R^8$ and B are as defined in general formula I, in the presence of a coupling reagent (e.g. 1,3-dicyclohexylcarbodiimide). Acid chlorides of general formula XXI, acid anhydrides of general formula XXII and carboxylic acids of general formula XIII may be prepared from carbonyl derivatives of general formula XIX wherein $R^4$ is hydrogen by procedures known to those skilled in the art.

The appropriate solvents employed in the above reactions are solvents wherein the reactants are soluble but do not react with the reactants. The preferred solvents vary from reaction to reaction and are readily ascertained by one of ordinary skill in the art.

Compounds of general formulae II, III and IV are valuable intermediates in the preparation of compounds of general formula I, as are other novel compounds specifically or generically disclosed herein. According to a third aspect of the invention, there is therefore provided a compound of general formula II. According to a fourth aspect of the invention, there is provided a compound of general formula III. According to a fifth aspect of the invention, there is provided a compound of general formula IV.

This invention also relates to a method of treatment for patients (or animals including mammalian animals raised in the dairy, meat, or fur trade or as pets) suffering from disorders or diseases which can be attributed to PAF as previously described, and more specifically, a method of treatment involving the administration of PAF antagonists of general formula I as the active ingredient. In addition to the treatment of warm blooded animals such as mice, rats, horses, cattle, pigs, sheep, dogs, cats, etc., the compounds of the invention are effective in the treatment of humans.

According to a sixth aspect of the invention there is provided a compound of general formula I for use in human or veterinary medicine particularly in the management of diseases mediated by PAF; compounds of general formula I can be used among other things to reduce inflammation and pain, to correct respiratory, cardiovascular, and intravascular alterations or disorders, and to regulate the activation or coagulation of platelets, to correct hypotension during shock, the pathogenesis of immune complex deposition and smooth muscle contractions.

According to an seventh aspect of the invention there is provided the use of a compound of general formula I in the preparation of an agent for the treatment of PAF-mediated diseases; and/or the treatment of inflammation such as rheumatoid arthritis, osteoarthritis and eye inflammation, cardiovascular disorder, thrombocytopenia, asthma, endotoxin shock, glomerulonephritis, immune regulation, gastric ulceration, transplant rejection, psoriasis and cerebral, myocardial and renal ischemia.

Compounds of general formula (I) may be administered orally, topically, parenterally, by inhalation spray or rectally in dosage unit formulations containing conventional non-toxic pharmaceutically acceptable carriers, adjuvants and vehicles. The term parenteral as used herein includes subcutaneous injections, intravenous, intramuscular, intrasternal injection or infusion techniques.

According to an eighth aspect of the invention there is provided a pharmaceutical or veterinary formulation comprising a compound of general formula I and a pharmaceutically and/or veterinarily acceptable carrier. One or more compounds of general formula I may be present in association with one or more non-toxic pharmaceutically and/or veterinarily acceptable carriers and/or diluents and/or adjuvants and if desired other active ingredients. The pharmaceutical compositions containing compounds of general formula I may be in a form suitable for oral use, for example, as tablets, troches, lozenges, aqueous or oily suspensions, dispersible powders or granules, emulsion, hard or soft capsules, or syrups or elixirs.

Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin, or olive oil.

Aqueous suspensions contain the active materials in admixture with excipients suitable for the manufacture of aqueous suspensions. Such excipients are suspending agents, for example sodium carboxymethylcellulose, methylcellulose, hydroxypropylmethylcellulose, sodium alginate, polyvinylpyrrolidone, gum tragacanth and gum acacia; dispersing or wetting agents may be a naturally-occurring phosphatide, for example lecithin, or condensation products of an alkylene oxide with fatty acids for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl p-hydroxybenzoate, one or more coloring agents, one or more flavoring agents, and one or more sweetening agents, such as sucrose or saccharin.

Oily suspensions may be formulated by suspending the active ingredients in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavoring agents may be added to provide a palatable oral preparations. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

Pharmaceutical compositions of the invention may also be in the form of oil-in-water emulsions. The oily phase may be a vegetable oil, for example olive oil or arachis oil, or a mineral oil, for example liquid paraffin or mixtures of these. Suitable emulsifying agents may be naturally-occurring gums, for example gum acacia or gum tragacanth, naturally-occurring phosphatides, for example soy bean, lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening and flavoring agents.

Syrups and elixirs may be formulated with sweetening agents, for example glycerol, propylene glycol, sorbitol or sucrose. Such formulations may also contain a demulcent, a preservative and flavoring and coloring agents. The pharmaceutical compositions may be in the form of a sterile injectable aqueous or oleaginous suspension. This suspension may be formulated according to the known art using those suitable dispersing or wetting agents and suspending agents which have been mentioned above. The sterile injectable preparation may also be a sterile injectable solution or suspension in a non-toxic parentally acceptable diluent or solvent, for example as a solution in 1,3-butane diol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono-or diglycerides. In addition, fatty acids such as oleic acid find use in the preparation of injectables.

The compounds of general formula I may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials are cocoa butter and polyethylene glycols.

For topical application to the skin compounds of general formula I may be made up into a cream, ointment, jelly, solution or suspension etc. Cream or ointment formulations that may be used for the drug are conventional formulations well known in the art, for example, as described in standard text books of pharmaceutics such as the British Pharmacopoeia.

For topical applications to the eye, compounds of general formula I may be made up into a solution or suspension in a suitable sterile aqueous or non-aqueous vehicle. Additives, for instance buffers, preservatives including bactericidal and fungicidal agents, such as phenyl mercuric acetate or nitrate, benzalkonium chloride or chlorohexidine, and thickening agents such as hypromellose may also be included.

Compounds of general formula I may be administered parenterally in a sterile medium. The drug depending on the vehicle and concentration used, can either be suspended or dissolved in the vehicle. Advantageously, adjuvants such as a local anaesthetic, preservative and buffering agents can be dissolved in the vehicle.

Compounds of general formula I may be used for the treatment of the respiratory tract by nasal or buccal administration of, for example, aerosols or sprays which can disperse the pharmacological active ingredient in the form of a powder or in the form of drops of a solution or suspension. Pharmaceutical compositions with powder-dispersing properties usually contain, in addition to the active ingredient, a liquid propellant with a boiling point below room temperature and, if desired, adjuncts, such as liquid or solid non-ionic or anionic surfactants and/or diluents. Pharmaceutical compositions in which the pharmacological active ingredient is in solution contain, in addition to this, a suitable propellant, and furthermore, if necessary, an additional solvent and/or a stabilizer. Instead of the propellant, compressed air can also be used, it being possible for this to be produced as required by means of a suitable compression and expansion device.

Dosage levels of the order of from about 0.1 mg to about 140 mg per kilogram of body weight per day are useful in the treatment of the above-indicated conditions (about 0.5 mg to about 7 g per patient per day).

For example, inflammation may be effectively treated by the administration of from about 0.01 to 50 mg of the compound per kilogram of body weight per day (about 1.0 mg to about 3.5 g per patient per day). The dosage employed for the topical administration will, of course, depend on the size of the area being treated. For the eyes each dose will be typically in the range from 10 to 100 mg of the drug.

The amount of active ingredient that may be combined with the carrier materials to produce a single dosage form will vary depending upon the host treated and the particular mode of administration. For example, a formulation intended for the oral administration of humans may contain from 0.5 mg to 5 g of active agent compounded with an appropriate and convenient amount of carrier material which may vary from about 5 to about 95 percent of the total composition. Dosage unit forms will generally contain between from about 1 mg to about 500 mg of an active ingredient.

It will be understood, however, that the specific dose level for any particular patient will depend upon a variety of factors including the activity of the specific compound employed, the age, body weight, general health, sex, diet, time of administration, route of administration, rate of excretion, drug combination and the severity of the particular disease undergoing therapy.

It has been found that the compounds of general formula I exhibit in vitro antagonistic activities with respect to PAF. Compounds of general formula I inhibit PAF-induced functions in both the cellular and tissue levels by changing the PAF binding to its specific receptor site. The ability of compounds of general formula I to inhibit the binding of PAF to its specific receptor binding site on human platelet plasma membranes was measured according to Pharmacological Example 1. The ability of compounds of general formula I to reverse the hypotension caused by an infusion of PAF in rats was measured according to Pharmacology Example 2.

The following examples illustrate the invention, but are not intended to limit the scope in any way.

The following abbreviations have been used in the Examples:
DCM—Dichloromethane
DIPE—Diisopropylether
DMF—Dimethylformamide
NBS—N-Bromosuccinimide
THF—Tetrahydrofuran
TLC—Thin layer chromatography
MPLC—Medium pressure liquid chromatography

EXAMPLE 1

(A) N-Methyl-N-L-leucinyl methyl ester 4-(3H-2-methylimidazo[4,5-c]pyridylmethyl)benzamide and (B) N-Methyl-N-L-leucinyl methyl ester 4-(1H-2-methylimidazo[4,5-c]pyridylmethyl)benzamide

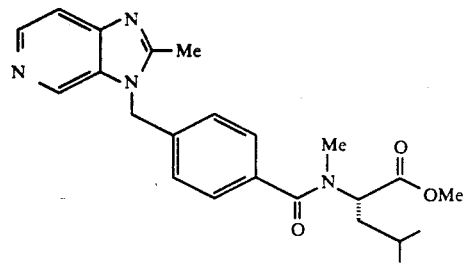

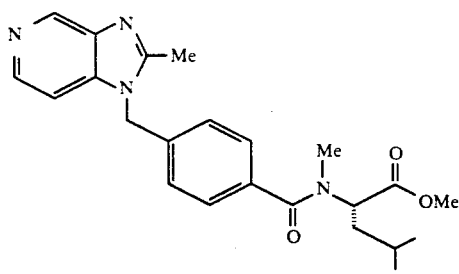

(a) 4-Bromomethylbenzoylchloride

To a solution of p-toluoyl chloride (155 g, 1 mol) in carbon tetrachloride (800 ml) and NBS (200 g, 1.1 mol) heated at reflux was added 2,2'-azobis(2-methylpropionitrile) (150 mg). The mixture was heated at reflux for 12 h and allowed to cool to room temperature. The white precipitate of succinimide that formed was separated and discarded. Concentration and subsequent crystallization (from DIPE at -15° C.) gave in five crops 4-bromomethylbenzoyl chloride (75 g, 32%) as a white crys solid.

m.p. 54° C.

delta$_H$ (250MHz, CDCl$_3$) 8.11 (2H, d, J 8.3 Hz), 7.54 (2H, d, J 8.3 Hz), 4.51 (2H, s).

(b) N-L-Leucinyl methyl ester 4-bromomethylbenzamide

To a solution of triethylamine (4.2 ml, 0.03 mol) in dry THF (100 ml) was added powdered L-leucine methyl ester hydrochloride (3.5 g, 0.019 mol) in one portion. The mixture was stirred at 0° C. for 1 h and a solution of 4-bromomethylbenzoyl chloride (4.15 g, 0.019 mol) in dry THF (20 ml) added in one portion. The mixture was stirred overnight at room temperature and the solvent removed under reduced pressure. Ethyl acetate (100 ml) was added and the mixture washed with water (100 ml) and brine (100 ml). The organics were dried over anhydrous magnesium sulphate, filtered and evaporated to give N-L-leucinyl methyl ester 4-bromomethylbenzamide (3.1 g, 66%) as a pale yellow oil (single spot by TLC [Rf 0.48]: silica, 1:2 ethyl acetate/hexane). delta$_H$ (250 MHz, CDCl$_3$) 7.76–7.70 (2H, m), 7.46 (2H, d, J 8.2 Hz), 6.58 (1H, d, J 8.4 Hz), 4.85 (1H, m), 4.61, 4.50 (2H, 2s), 3.78 (3H, s), 1.58–1.82 (3H, m), 0.99 (3H, d, J 5.8 Hz), 0.98 (3H, d, J 6.0 Hz).

(c) N-Methyl-L-leucinyl methyl ester 4-bromomethylbenzamide

To a stirred solution of N-L-leucinyl methyl ester 4-bromomethylbenzamide (2.0 g, 5.8 mmol) in dry THF (50 ml) under argon at 0° C. was added methyl iodide (1.6 g, 11.6 mmol) and sodium hydride (60% dispersion in oil: 0.25 g, 6.4 mmol). The reaction mixture was stirred overnight at room temperature, and the solvent removed under reduced pressure. Ethyl acetate (100 ml) was added and the mixture washed with water (100 ml) and brine (100 ml). The organics were dried over anhydrous magnesium sulphate, filtered and concentrated to give N-methyl-L-leucinyl methyl ester 4-bromomethylbenzamide (1.95 g, 93%) as a yellow oil (single spot by TLC [Rf 0.36]: silica, 1:2 ethyl acetate/hexane). delta$_H$ (250 MHz, CDCl$_3$) 7.42–7.34 (4H, m), 5.35 (0.6H, br t), 4.44 (2H, s), 3.99 (0.4H, m), 3.75 , 3.73 (3H, 2 s), 2.96 (1.2H, s), 2.89 (1.8H, s), 1.85–1.60 (3H, m), 1.0 (3.6H, br d), 0.85 (1.2H, br d), 0.64 (1.2H, br d).

(d) N-Methyl-N-L-leucinyl methyl ester 4-(3H-2-methylimidazo[4,5-c]pyridylmethyl)benzamide and N-methyl-N-L-leucinyl methyl ester 4-(1H-2-methylimidazo[4,5-c]pyridylmethyl)benzamide To a stirred solution of 2-methylimidazopyridine (0.72 g, 5.5 mmol) in dry THF (50 ml) and dry DMF (15 ml) under argon was added sodium hydride (60% dispersion in oil: 0.26 g, 6.6 mmol). The solution was left to stir for 1 h at room temperature, cooled to 0° C. and a solution of N-methyl-L-leucinyl methyl ester 4-bromomethylbenzamide (1.95 g, 5.5 mmol) in dry THF (αml) added dropwise. The reaction mixture was allowed to warm up to room temperature and stirred overnight. The solvent was removed under reduced pressure, ethyl acetate (100 ml) added and the mixture washed with water (60 ml) and brine (60 ml). The organics were dried over anhydrous magnesium sulphate, filtered and concentrated and the residue chromatographed over silica gel (10% methanol in DCM) to give a mixture of regioisomers (A) and (B). Separation of the two regioisomers was accomplished by MPLC (silica gel, 5% methanol in DCM) to give (A) N-methyl-N-L-leucinyl methyl ester 4-(3H-2-methylimidazo[4,5-c]pyridylmethyl)benzamide (120 mg, 10%) followed by (B) N-methyl-N-L-leucinyl methyl ester 4-(1H-2-methylimidazo[4,5-c]pyridylmethyl)benzamide (120 mg, 10%).

(A) N-Methyl-N-L-leucinyl methyl ester 4-(3H-2-methylimidazo[4,5-c]pyridylmethyl)benzamide Yellow oil.

delta$_H$ (250 MHz, CDC13) 8.63 (1H, s), 8.42 (1H, d, J 5.5 Hz), 7.62 (1H, d, J 5.3 Hz), 7.39 (2H, m), 7.09 (2H, d, J 7.8 Hz), 5.41 (2H, s), 5.35 (0.4H, m), 4.28 (0.6H, m), 3.72 (3H, s), 2.94 (1.2H, s), 2.84 (1.8H, s), 1.83 (1H, m), 1.77 (2H, m), 0.99 (1.8H, d, J 6.4 Hz), 0.96 (1.8H, d, J 6.3 Hz), 0.81 (1.2H, d, J 6.5 Hz), 0.56 (1.2H, d, J 6.4 Hz).

(B) N-Methyl-N-L-leucinyl methyl ester 4-(1H-2-methylimidazo[4,5-c]pyridylmethyl)benzamide Yellow oil.

[Analysis calculated for $C_{23}H_{28}N_4O_3 \cdot 1.2H_2O$ Requires C 64.23 H 7.12 N 13.03 Found C 64.12 H 6.81 N 12.65 i.r.(CHCl$_3$) 3015, 2395, 1630 cm$^{-1}$ delta$_H$ (250 MHz, CDCl$_3$) 9.00 (1H, s}, 8.34 (1H, d, J 5.5 Hz), 7.37 ,(2H, m), 7.14 (1H, d, J 5.3 Hz), 7.05 (2H, d, J 7.8 Hz), 5.34 (0.4H, m), 5.33 (2H, s), 4.27 (0.6H, m), 3.71 (3H, s), 2.93 (1.2H, s), 2.83 (1.8H, s), 2.56 (3H, s), 1.85–1.40 (3H, m}, 0.97 (1.8H, d, J 6.4 Hz), 0.95 (1.8H, d, J 6 3 Hz), 0.80 (1.2H, d, J 6.5 Hz), 0.57 (1.2H, d, J 6.3 Hz).

EXAMPLE 2

(A) N-Methyl-N-L-leucinyl ethyl ester 4-(3H-2-methylimidazo[4,5-c]pyridylmethyl)benzamide and (B) N-methyl-N-L-leucinyl ethyl ester 4-(1H-2-methylimidazo[4,5-c]pyridylmethyl)benzamide

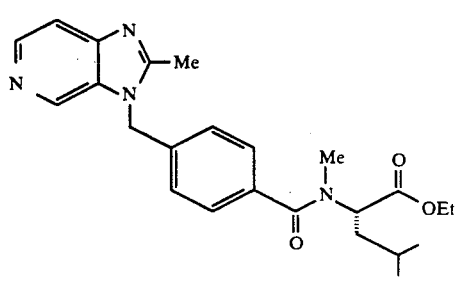

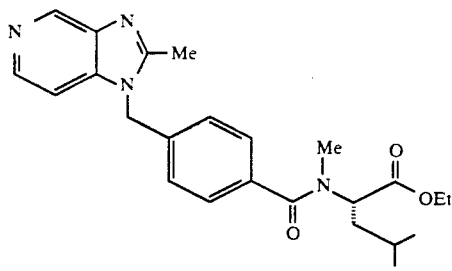

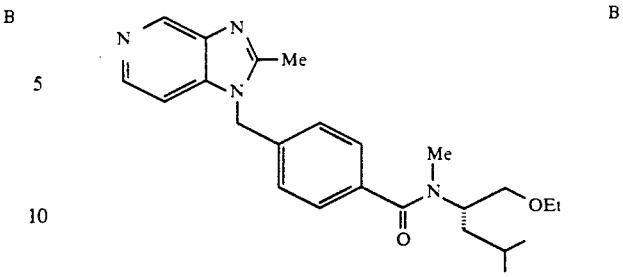

N-Methyl-N-L-leucinyl ethyl ester 4-(3H-2-methylimidazo[4,5-c]pyridylmethyl)benzamide and N-methyl-N-L-leucinyl ethyl ester 4-(1H-2-methylimidazo[4,5-c]pyridylmethyl)benzamide were prepared following the procedure of Example 1 utilizing L-leucine ethyl ester hydrochloride in lieu of L-leucine methyl ester hydrochloride.

(A) N-Methyl-N-L-leucinyl ethyl ester 4-(3H-2-methylimidazo[4,5-c]pyridylmethyl)benzamide Yellow oil (6% yield for last step after chromatography). i.r.(CHCl₃) 3015, 2395, 1630 cm⁻¹ delta$_H$ (250 MHz, CDCl₃) 8.66 (1H, s}, 8.45 {1H, d, J 5.5 Hz), 7.65 (1H, d, J 5.5 Hz), 7.43 (2H, d, J 7.9 Hz), 7.12 (2H, d, J 7.5 Hz), 5.43 (2H, s), 5.36 (0.45H, m), 4.38 (0.55H, m), 4.25 (2H, q, J 7.1 Hz), 2.96 ( 1.4H, s), 2.85 (1.6H, s), 1.84 (1H, m), 1.67 (2H, m), 1.31 (3H, t, J 7.1 Hz), 0.99 (3.6H, d, J 6.1 Hz), 0.83 (1.2H, d, J 6.3 Hz), 0.61 (1.2H, d, J 6.3 Hz).

(B) N-Methyl-N-L-leucinyl ethyl ester 4-(1H-2-methylimidazo[4,5-c]pyridylmethyl)benzamide Yellow oil (6% yield for last step after chromatography).

Analysis calculated for C24H30N4O3.1.0H2O Requires C 65.45 H 7.09 N 12.49 Found C 65.45 H 7.09 N 12.49 delta$_H$ (250 MHz, CDCl₃) 8.98 (1H, s), 8.31 (1H, d, J 5.5 Hz), 7.35 (2H, d, J 7.8 Hz), 7.12 (1H, d, J 4.9 Hz), 7.03 (2H, d, J 7.7 Hz), 5.30 (2H, s), 5.26 (0.4H, m), 4.32 (Q.6H, m), 4.19 (2H, q, J 7.1 Hz), 2.91 (1.2H, s), 2.81 (1.8H, s), 2.54 (3H, s), 1.77 (1H, m), 1.62 (2H, m), 1.26 (3H, t, J 7.1 Hz), 0.94 (3.6H, d, J 5.1 Hz), 0.78 (1.2H, d, J 6.5 Hz), 0.56 (1.2H, d, J 6.3 Hz).

EXAMPLE 3

(A) N-Methyl-N-L-leucinol ethyl ether 4-(3H-2-methylimidazo[4,5-c]pyridylmethyl)benzamide and (B) N-methyl-N-L-leucinol ethyl ether 4-(1H-2-methylimidazo[4,5-c]pyridylmethyl)benzamide N-Methyl-N-L-leucinol ethyl ether 4-(3H-2-methylimidazo[4,5-c]pyridylmethyl)benzamide and N-methyl-N-L-leucinol ethyl ether 4-(1H-2-methylimidazo[4,5-c]pyridylmethyl)benzamide were prepared following the procedure of Example 1 utilizing L-leucine ethyl ether in lieu of L-leucine methyl ester hydrochloride.

(A) N-Methyl-N-L-leucinol ethyl ether 4-(3H-2-methylimidazo[4,5-c]pyridylmethyl)benzamide Pale yellow oil (6% yield for final step after chromatography)

i.r. (CHCl₃) 3005, 2395, 1610 cm⁻¹ delta$_H$ (250 MHz, CDCl₃) 8.65 (1H, br s), 8.34 (1H, br s), 7.62 (1H, d, J 5.4 Hz), 7.46 (1H, d, J 8.2 Hz), 7.35 (1H, d, J 8.1 Hz), 7.08 (2H, m), 5.40 (2H, s), 4.94 (0.4H, m), 3.85 (0.6H, m), 3.60–3.23 (4H, m), 2.89 (1.8H, s), 2.75 (1.2H, s), 2.61 (1.2H, s), 2.59 (1.8H, s) 1.60–0.80 (3H, m), 1.16 (3H, t, J 6.9 Hz), 0.97 (1 2H, d, J 6.3 Hz), 0 95 (1.2H, d, J 6.3 Hz), 0.76 (1.8H, d, J 6.3 Hz), 0.55 (1.8H, d, J 6.3 Hz).

(B) N-Methyl-N-L-leucinol ethyl ether 4-(1H-2-methylimidazo[4,5-c]pyridylmethyl)benzamide Yellow oil (5% yield for final step after chromatography).

i.r. (CHCl₃) 3005, 2395, 1610 cm⁻¹ delta$_H$ (250 MHz, CDCl₃) 9.01 (1H, s), 8.34 (1H, d, J 5.2 Hz), 7.45 (1H, d, J 8.1 Hz), 7.34 (1H, d, J 8 1 Hz), 7.16.(1H, d, J 5.2 Hz), 7.03 (2H, d, J 8.1 Hz), 5.32 (2H, s), 4.95 (0.4H, m), 3.86 (0.6H, m), 3.60–3.22 (4H, m), 2.89 (1.8H, s), 2.75 (1.2H, s), 2.58 (1.2H, s), 2.57 (1.8H, s), 1.60–1.00 (3H, m), 1.16 (3H, t, J 7.0 Hz), 0.97 (1.2H, d, J 6.2 Hz), 0.94 (1.2H, d, J 6.2 Hz), 0.76 (1.8H, d, J 6.2 Hz), 0.55 (1.8H, d, J 6.2 Hz).

COMPARATIVE EXAMPLE

N-Cyclohexyl-N-methyl 4-(1H-imidazo[4,5-c]pyridylmethyl)benzamide

This compound is not within the scope of the invention: It has been included here as a comparative example. This compound was described in EP-A-0260613.

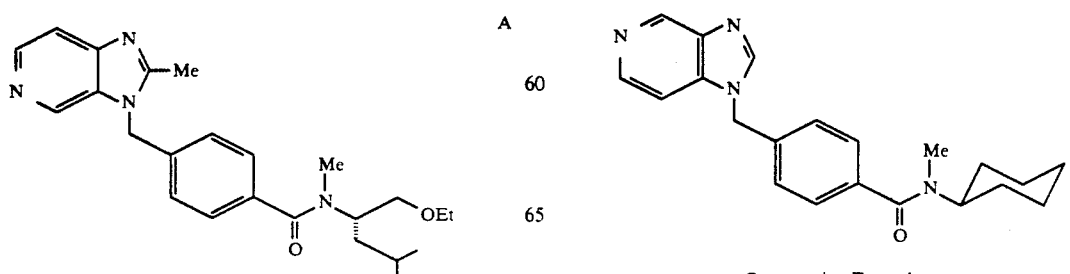

Comparative Example

Sodium bis(trimethylsilyl)amide (22 ml of 1 M solution in THF) was added to a stirred solution of imidazo[4,5-c]pyridine (2.60 g, 0.02 mol) in dry THF (200 ml) under argon. A fine white precipitate formed. After 90 m the mixture was treated with purified N-cyclohexyl-N-methyl 4-bromomethylbenzamide (6.20 g, 0.02 mol) dissolved in dry THF (50 ml). The mixture was allowed to warm to ambient temperature and stirred overnight. Methanol (1 ml) was added, followed by water and the product extracted using ethyl acetate (3×150 ml). The combined organic layers were washed with water (2×100 ml), dried over $K_2CO_3$ and the solvent removed to give the crude product. Flash chromatography (flash silica: 10% methanol in ethyl acetate) followed by repeated fractional crystallization (6 times from ethyl acetate/DIPE) gave the desired regioisomer N-cyclohexyl-N-methyl 4-(1H-imidazo[4,5-c]pyridin-1-ylmethyl)benzamide (0.39 g, 5%) as an off white crystalline solid.

m.p. 121°–123° C.

Analysis calculated for $C_{21}H_{24}N_4O.0.6H_2O$ Requires C 70.21 H 7.07 N 15.60

Found C 70.08 H 6.91 N 15.37 i.r. (KBr), 1615 cm$^{-1}$ $delta_H$ (250 MHz, $CDCl_3$) 9.17 (1H, s), 8.42 (1H, d, J 5.6 Hz), 8.03 (1H, s), 7.37 (2H, d, J 7.8 Hz), 7.27–7.19 (3H, m), 5.42 (2H, s), 4.50, 3.37 (1H, 2bm), 2.96, 2.76 (3H, 2vs), 2.05–1.02 (10H, bm).

Pharmacology Example 1

The inhibition of $^3$H-PAF binding to human platelet plasma membrane by compounds of general formula I was determined by isotopic labelling and filtration techniques. Platelet concentrates were obtained from a hospital blood bank. These platelet concentrates (500–2500 ml.) were centrifuged at 800 rpm for 10 minutes in a SORVALL RC3B centrifuge to remove the red blood cells present. (The word SORVALL is a trade mark.) The supernatant was subsequently centrifuged at 3,000 rpm in a SORVALL RC3B centrifuge to pellet the platelets present. The platelet rich pellets were resuspended in a minimum volume of buffer (150 mM NaCl, 10 mM Tris, 2 mM EDTA, pH 7.5) and layered onto Ficoll-Paque gradients, 9 ml platelet concentrate to 2 ml Ficoll, and centrifuged at 1,900 rpm for 15 minutes in a SORVALL RT6000 centrifuge. This step removes the residual red blood cells and other nonspecific material such as lymphocytes from the preparation. The platelets which form a band between the plasma and the Ficoll were removed, resuspended in the above buffer and centrifuged at 3,000 rpm for 10 minutes in a SORVALL RT6000 centrifuge. The pelleted platelets were resuspended in buffer (10 mM Tris, 5mM $MgCl_2$, 2 mM EDTA, pH 7.0), snap freezed in liquid N2 and allowed to thaw slowly at room temperature in order to lyse the platelets. The latter step was repeated at least 3 times to ensure proper lysis. The lysed platelets were centrifuged at 3,000 rpm for 10 minutes in a SORVALL RT6000 centrifuge and resuspended in buffer. The latter step was repeated twice in order to remove any cytoplasmic proteins which may hydrolyse the platelet activating factor (PAF) receptor. The prepared platelet membranes may be stored at −70° C. After thawing the prepared membranes were centrifuged in a SORVALL RT6000 at 3,000 rpm for 10 minutes and resuspended in assay buffer.

The assay was conducted by preparing a series of Tris-buffered solutions of the selected antagonist of predetermined concentrations. Each of these solutions contained $^3$H-PAF (0.5 nM; 1-O-[$^3$H]octadecyl-2-acetyl-sn-glycero-3-phosphoryl choline with a specific activity of 132 Ci/mmol), unlabelled PAF (1000 nM), a known amount of the test antagonist, and a sufficient amount of Tris-buffer solution (10mM Tris, 5mM $MgCl_2$, pH 7.0, 0.25% BSA) to make the final volume 1 ml. Incubation was initiated by the addition of 100 μg of the isolated membrane fraction to each of the above solutions at 0° C. Two control samples, one (C1) which contained all the ingredients described above except the antagonist and the other (C2) contains C1 plus a 1000-fold excess of unlabelled PAF, were also prepared and incubated simultaneously with the test samples. After 1 hour incubation, each solution was filtered rapidly under through a WHATMAN GF/C glass fiber filter in order to separate unbound PAF from bound PAF. (The word WHATMAN is a trade mark.) The residue in each case was rapidly washed 4 times with 5 ml cold (4° C.) Tris-buffer solution. Each washed residue was dried under vacuum on a sampling manifold and placed into vials containing 20 ml of OPTIPHASE MP scintillation fluid and the radioactivity counted in a liquid scintillation counter. (The word OPTIPHASE is a trade mark.) Defining the counts for total binding with antagonist from a test sample as "TBA"; the counts for total binding from the control sample C1 as "TB"; and the counts for nonspecific binding from the control sample C2 as "NSB", the percent inhibition of each test antagonist can be determined by the following equation:

$$\%Inhibition = [(TB - TBA)/SB] \times 100$$

where the specific binding $SB = TB - NSB$

Table 1 lists results from this assay for inhibition of $^3$H-PAF receptor binding for illustrative examples of the compounds of this invention. Also presented . Table 1 is the result for a comparative example (N-cyclohexyl-N-methyl 4-(1H-imidazo- [4,5-c]pyridin-1-ylmethyl))benzamide. This compound (a PAF antagonist described in EP-A-02606130) is not within the scope of the invention.

TABLE 1

| Results for inhibition of $^3$H-PAF receptor binding | |
|---|---|
| Example | Inhibition of $^3$H-PAF binding $IC_{50}$ nM |
| 2 (B) | 10 |
| Comparative Example | 10,000 |

Pharmacology Example 2

The activity of the compounds of general formula I is also demonstrated in vivo by their ability to reverse the hypotension caused by an infusion of PAF in rats. Male Sprague-Dawley rats (300–350 gms) were anaesthetised with a mixture of sodium pentobarbitone, 22.5 mg.kg$^{-1}$ and thiopental 62.5 mg.kg$^{-1}$. Through a midline incision in the neck, the trachea was cannulated and the animals breathed spontaneously. A carotid artery was cannulated for the measurement of blood pressure and this signal was used to trigger a rate meter to measure heart rate. Both jugular veins were cannulated: one for the infusion of PAF and the other for the bolus administration of test compounds.

PAF, 100 ng.kg$^{-1}$·min$^{-1}$ was infused i.v. until a sustained fall in mean blood pressure of 50 mmHg was achieved. Test compounds were administered i.v. as a bolus and resulted in a dose dependent reversal of the PAF induced hypotension. The peak of this reversal was measured and the dose to cause a 50% reversal of the hypotensive PAF response ($ED_{50}$) calculated by straight line interpolation and the results are presented in Table 2. Also presented in Table 2 is the result for a comparative example (N-cyclohexyl-N-methyl 4-(1H-imidazo[4,5-c]pyridin-1-ylmethyl)benzamide. This compound (a PAF antagonist described in EP-A-02606130) is not within the scope of the invention.

TABLE 2

Results for inhibition of PAF-induced hypotension in the rat

| Example | $ED_{50}$ (μg/kg i. v.) |
|---|---|
| 2 (B) | 5 |
| 3 (B) | 6 |
| Comparative Example | 150 |

What is claimed is:
1. A compound of formula I;

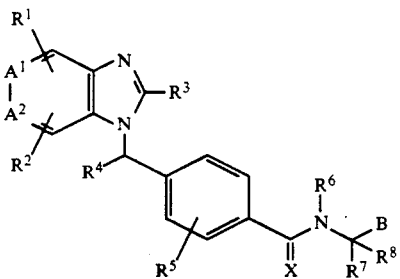

wherein:
$A^1$ is =N—, =CH— or =$CR^1$—;
$A^2$ is —N=, —CH= or —$CR^2$=;
each of $R^1$ and $R^2$ independently represents hydrogen, $C_1$-$C_6$ alkyl, $C_2$-$C_6$ alkenyl, halogen, CN, $CO_2H$, $CO_2C_1$-$C_6$ alkyl, $CONH_2$, CHO, $CH_2OH$, $CF_3$, $C_1$-$C_6$ alkoxy, $C_1$-$C_6$ alkylthio, $SOC_1$-$C_6$ alkyl, $SO_2C_1$-$C_6$ alkyl, $NH_2$, NHCOMe or $NO_2$ or $R^1$ and $R^2$ together with the carbon atoms to which they are attached form a fused phenyl ring;
$R^3$ represents hydrogen, $C_1$-$C_6$ alkyl, $C_2$-$C_6$ alkenyl, Cl-C6 alkoxy, $C_1$-$C_6$ alkylthio, $C_1$-$C_6$ alkoxy ($C_1$-$C_6$ alkyl), $C_1$-$C_6$ alkylthio ($C_1$-$C_6$ alkyl), $CF_3$, phenyl ($C_1$-$C_6$ alkyl), $C_3$-$C_8$ cycloalkyl or thiophenyl;
$R^4$ represents hydrogen, $C_1$-$C_6$ alkyl, $C_2$-$C_6$ alkenyl, $CO_2C_1$-$C_6$ alkyl, $C_1$-$C_6$ alkylthio, $C_1$-$C_6$ alkylthio ($C_1$-$C_6$ alkyl), $C_1$-$C_6$ alkoxy ($C_1$-$C_6$ alkyl), phenyl ($C_1$-$C_6$ alkyl) or thiophenyl;
$R^5$ represents hydrogen, $C_1$-$C_6$ alkyl, $C_2$-$C^6$ alkenyl, halogen or $C_1$-$C_6$ alkoxy;
X represents an oxygen or a sulphur atom;
$R^6$ represents hydrogen, $C_1$-$C_6$ alkyl, $C_2$-$C_6$ alkenyl, $COC_1$-$C_6$ alkyl, $C_1$-$C_6$ alkoxy ($C_1$-$C_6$ alkyl), $C_3$-$C_8$ cycloalkyl, $C_4$-$C_8$ cycloalkenyl or a group D wherein D represents a group:

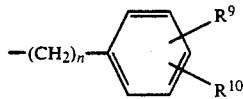

wherein n is an integer from 0 to 3, and each of $R^9$ and $R^{10}$ is independently hydrogen, $C_1$-$C_6$ alkyl, $C_2$-$C_6$ alkenyl, halogen, CN, $CO_2H$, $CO_2C_1$-$C_6$ alkyl, $CONH_2$, CHO, $CH_2OH$, $CF_3$, $C_1$-$C_6$ alkoxy, $C_1$-$C_6$ alkylthio, $SOC_1$-$C_6$ alkyl, $SO_2C_1$-$C_6$ alkyl, $NH_2$ or NHCOMe;

or $R^6$ together with $R^7$ and the atoms to which they are attached forms a 5 to 8 membered nitrogen-containing heterocyclic ring;

each of $R^7$ and $R^8$ independently represents hydrogen, $C_1$-$C_6$ alkyl, $C_2$-$C_6$ alkenyl, $CO_2C_1$-$C_6$ alkyl ($C_1$-$C_6$ alkyl), $C_1$-$C_6$ alkylthio ($C_1$-$C_6$ alkyl), $C_1$-$C_6$ alkoxy ($C_1$-$C_6$ alkyl), benzoxy ($C_1$-$C_6$ alkyl), a side chain of a naturally occurring amino acid or a group D as defined above;

or $R^7$ together with $R^8$ and the atoms to which they are attached forms a 5 to 8 membered nitrogen-containing heterocyclic ring;

or $R^7$ and $R^8$ together with the carbon atom to which they are attached form a $C_3$-$C_8$ cycloalkyl ring;

B represents a) a $ZR^{11}$ group wherein Z is —C(=O)—, —C(=O)O—, —$CH_2O$—, —$CH_2OC$(=O)—, —C(=S)—, —C(=S)O— or —$CH_2S$— and $R^{11}$ is $C_1$-$C_{18}$ alkyl, $C_2$-$C_{18}$ alkenyl, $C_1$-$C_6$ alkoxy ($C_1$-$C_6$ alkyl), $C_1$-$C_6$ alkylthio ($C_1$-$C_6$ alkyl), $C_1$-$C_6$ alkoxy ($CH_2CH_2OCH_2CH_2$), $C_3$-$C_8$ cycloalkyl, $C_4$-$C_8$ cycloalkenyl, pyridyl or a group D as defined above;

b) a $CH_2NR^{12}R^{13}$ group or a $CONR^{12}R^{13}$ group wherein each of $R^{12}$ and $R^{13}$ is independently hydrogen, $C_1$-$C_6$ alkyl, $C_3$-$C_8$ cycloalkyl, pyridyl, a group D as defined above or $R^{12}$ and $R^{13}$ together with the nitrogen atom to which they are attached form a 5 to 8 membered nitrogen-containing heterocyclic ring;

c) a 5- or 6-membered aromatic heterocyclic ring containing one or more heteroatoms selected from nitrogen, oxygen and sulphur and the ring may be optionally substituted with one or more substituents selected from $C_1$-$C_6$ alkyl, $C_1$-$C_6$ alkoxy, halogen, $CF_3$ and CN;

2. A compound as claimed in claim 1, in which $A^1$ represents =N— or =CH—.

3. A compound as claimed in claim 1, wherein $A^2$ represents —N= or —CH=.

4. A compound as claimed in claim 1, wherein $R^1$ represents a hydrogen atom.

5. A compound as claimed in claim 1, wherein $R^2$ represents a hydrogen atom.

6. A compound as claimed in claim 1, wherein $R^3$ represents a $C_1$-$C_6$ alkyl group.

7. A compound as claimed in claim 1, wherein $R^4$ represents a hydrogen atom.

8. A compound as claimed in claim 1, wherein $R^5$ represents a hydrogen atom.

9. A compound as claimed in claim 1, wherein X represents an oxygen atom.

10. A compound as claimed in claim 1, wherein $R^6$ represents a $C_1$-$C_6$ alkyl group.

11. A compound as claimed in claim 1, wherein $R^7$ represents the side chain of a naturally occurring amino acid.

12. A compound as claimed in claim 1, wherein $R^8$ represents a hydrogen atom.

13. A compound as claimed in claim 11, wherein the stereochemistry of the carbon to which $R^7$ and $R^8$ are attached is the same as that of the naturally occurring amino acid.

14. A compound as claimed in claim 1, wherein B represents a $ZR^{11}$ group.

15. A compound as claimed in claim 14, wherein Z represents a —C(=O)O— group or a —CH$_2$O— group.

16. A compound as claimed in claim 14, wherein $R^{11}$ represents a $C_1$–$C_{18}$ alkyl group.

17. N-Methyl-L-leucinyl methyl ester 4-(3H-2-methylimidazo[4,5-c]pyrid-3ylmethyl)benzamide, N-Methyl-L-leucinyl methyl ester 4-(1H-2-methylimidazo]4,5-c]pyrid-1-ylmethyl)benzamide, N-Methyl-L-leucinyl ethyl ester 4-(1H-2-methylimidazo]4,5-c]pyrid-3-ylmethyl)benzamide, N-Methyl-L-leucinyl ethyl ester 4-(1H-2-methylimidazo]4,5-c]pyrid-1-ylmethyl)benzamide, N-Methyl-L-leucinol ethyl ester 4-(3H-2-methylimidazo(4,5-c]pyrid-3-ylmethyl)benzamide, N-Methyl-L-leucinol ethyl ether 4-(1H-2-methylimidazo[4,5-c]pyrid-1-ylmethyl)benzamide, or a salt of such a compound.

18. A pharmaceutical or veterinary composition comprising a compound as claimed in claim 1 and a pharmaceutically or veterinarily acceptable carrier.

19. A method for the management of diseases or disorders mediated by platelet-activating factor comprising treating an animal in need thereof with an effective amount of a compound of claim 1.

* * * * *